(12) United States Patent
McCrickard et al.

(10) Patent No.: US 9,494,504 B2
(45) Date of Patent: Nov. 15, 2016

(54) DUAL COMPONENT DENSITY SAMPLER APPARATUS

(71) Applicants: James P. McCrickard, Racine, WI (US); Ronald G. Peterson, Racine, WI (US); Thomas L. Beck, Union Grove, WI (US);
(Continued)

(72) Inventors: James P. McCrickard, Racine, WI (US); Ronald G. Peterson, Racine, WI (US); Thomas L. Beck, Union Grove, WI (US); Michael A. Macdonald, Racine, WI (US); Michael D. Dry, Racine, WI (US)

(73) Assignee: Unico, Inc., Franksville, WI (US)

( * ) Notice: Subject to any disclaimer, the term of this patent is extended or adjusted under 35 U.S.C. 154(b) by 0 days.

(21) Appl. No.: 14/955,262

(22) Filed: Dec. 1, 2015

(65) Prior Publication Data
US 2016/0178499 A1     Jun. 23, 2016

Related U.S. Application Data

(60) Provisional application No. 62/092,995, filed on Dec. 17, 2014.

(51) Int. Cl.
| | | |
|---|---|---|
| *G01N 9/32* | (2006.01) | |
| *B01D 17/02* | (2006.01) | |
| *G01F 1/84* | (2006.01) | |

(52) U.S. Cl.
CPC ............... *G01N 9/32* (2013.01); *B01D 17/02* (2013.01); *G01F 1/84* (2013.01)

(58) Field of Classification Search
CPC .............. G01N 9/00; G01N 9/36; G01N 9/32; G01N 2291/02818; B01D 17/02; B01D 17/045; B01D 17/0217; B01D 17/0214; B01D 17/0208; G01F 1/84
USPC ................................................ 73/32 R, 32 A
See application file for complete search history.

(56) References Cited

U.S. PATENT DOCUMENTS

| | | |
|---|---|---|
| 2004/0094227 A1 | 5/2004 | Few |
| 2007/0131283 A1 | 6/2007 | Rogers et al. |
| 2009/0139345 A1* | 6/2009 | Xie .................. G01F 15/02 |
| | | 73/861.04 |

(Continued)

FOREIGN PATENT DOCUMENTS

| | | |
|---|---|---|
| CN | 203976539 U * | 12/2014 |
| KR | 101413302 B1 * | 6/2014 |

*Primary Examiner* — Hezron E Williams
*Assistant Examiner* — Marrit Eyassu
(74) *Attorney, Agent, or Firm* — Reinhart Boerner Van Deuren P.C.

(57) ABSTRACT

A dual component density sampler determines at least one of a density of water and a density of oil in a mixture of oil and water extracted from an oil well during production. A three-way valve is coupled to the oil well, with the three-way valve having a first output port and second output port. A dual-in-single-out manifold is coupled to the first output port. A segregation tank separates the water and oil, and has an entrance tank and exit tank. An entrance of the entrance tank is coupled to the second output port, and an exit of the entrance tank is coupled to an entrance end of the exit tank. An exit end of the exit tank is coupled to the dual-in-single-out manifold. A coriolis meter is coupled to the dual-in-single-out manifold, and is configured to selectively measure a density of the fluid mixture, the oil, and the water.

20 Claims, 6 Drawing Sheets

(71) Applicants: Michael A. Macdonald, Racine, WI (US); Michael D. Dry, Racine, WI (US)

(56) References Cited

U.S. PATENT DOCUMENTS

| | | | | |
|---|---|---|---|---|
| 2009/0199653 A1* | 8/2009 | Kitami | ................. | G01F 1/74 |
| | | | | 73/861.04 |
| 2011/0290035 A1 | 12/2011 | Wee et al. | | |
| 2012/0111571 A1* | 5/2012 | Eriksen | ............. | B01D 17/06 |
| | | | | 166/336 |
| 2014/0083950 A1* | 3/2014 | Usher | ................. | C02F 1/40 |
| | | | | 210/739 |
| 2014/0158897 A1 | 6/2014 | Troxler et al. | | |

\* cited by examiner

DUAL COMPONENT DENSITY SAMPLER APPARATUS

CROSS-REFERENCE TO RELATED PATENT APPLICATIONS

This patent application claims the benefit of U.S. Provisional Patent Application No. 62/092,995, filed Dec. 17, 2014, the entire teachings and disclosure of which are incorporated herein by reference thereto.

FIELD OF THE INVENTION

This present invention relates generally to oil well production, and more specifically to a system that separates oil and water components, determines the densities of the components under oil well production conditions and determines the net oil output using those component densities.

BACKGROUND OF THE INVENTION

There are many reasons that oil well operators want to know the amount of oil and the amount of water being extracted from the reservoir by the well. The fluid typically extracted is a mixture of oil, water, and entrained gas. The gas in the fluid can be removed by a gas separator as is well known in the industry. Accurately determining the amounts of oil and water in the fluid mixture is more difficult.

It is known to measure the density of the fluid produced by the well, as well as the pressure and temperature of the fluid, to calculate in real time the relative amounts of water and oil being produced. Then, using methods well known in the art to adjust for temperature and pressure differences, one can determine the amounts of oil and water produced at a standard temperature and pressure. To do so, however, requires that the densities of each component, at a known pressure and temperature, be known values.

One method of determining the densities of the components is to remove a sample from the production flow and to send the sample to have oil and water densities determined in a laboratory setting. Laboratory analysis is usually done at standard temperature and pressure. Such removal presents several problems. The significant differences in pressures and temperature from production conditions can cause the measured densities to deviate so far from the production densities that the calculations compensating for changes in temperature and pressure become less accurate. Also, conditions within the subterranean environment can change over time. For instance, the fluid reservoir may be treated with steam or chemicals or the flow within the reservoir may change from one segment of the reservoir to another resulting in a potential change of density of one or both of the components. Taking a sample and sending it to a laboratory on a frequent enough basis to detect and account for such changes is burdensome enough that it is usually not done.

Using a coriolis meter in the production flow, which measures the density of the fluid passing through it as part of its normal operation, to determine the densities of the individual components would address these problems. However, some past efforts to do this have involved interrupting the operation of the pump for significant portions of time to allow the fluid to separate into components within the production tubing and thereby reduced the total fluid output of the well. The apparatus of the present invention overcomes these limitations.

It would therefore be desirable to have an apparatus that could provide for the sampling of component densities, and which would be constructed to be both reliable and long-lasting, and which would overcome many of the disadvantages and limitations of the background art discussed above. Additionally, it would be desirable if the apparatus required little or no maintenance to be provided by the user throughout its operating lifetime. In order to enhance the market appeal of the apparatus of the present disclosure, it should also be of inexpensive construction to thereby afford the apparatus the broadest possible market.

Embodiments of the present invention provide such a component density sampling apparatus. These and other advantages of the invention, as well as additional inventive features, will be apparent from the description of the invention provided herein.

SUMMARY OF THE INVENTION

There is disclosed a dual component density sampler apparatus structured to determine a density of the water component and a density of an oil component of a fluid mixture of oil and water. The fluid mixture of oil and water is extracted from an oil well. The determination of the density of the water and oil components are obtained while maintaining the dual component density sampler apparatus in a production condition. In other words, the temperature and pressure of the fluid being extracted is maintained when in the apparatus.

The dual component density sampler apparatus includes a three-way valve, a dual-in-single-out manifold, a segregation tank apparatus, and a coriolis meter. The dual-in-single-out manifold is coupled to the first output port of a three-way valve.

In a particular embodiment, the three-way valve is coupled to the oil well by appropriate piping, which may include a gas separator apparatus, during production flow of the fluid from the oil well. The three-way valve includes a first output port and a second output port.

The segregation tank apparatus is configured for separating a water component and an oil component of the fluid mixture being extracted from the oil well. The segregation tank apparatus includes an entrance tank and an exit tank. An entrance end of the entrance tank is coupled to the second output port of the three-way valve with an exit end of the entrance tank is coupled to an entrance end of the exit tank. The exit end of the exit tank is coupled to the dual-in-single-out manifold. The entrance tank and exit tank of the segregation tank apparatus may be structured with different volumes. In a specific embodiment, the entrance tank has a volume greater than that of the exit tank.

The coriolis meter may be coupled to the dual-in-single-out manifold and receives fluid, as determined by the setting of the three-way valve, from the first output port of the three-way valve or from the segregation tank apparatus. The coriolis meter selectively measures a density of the fluid mixture, the density of the oil component, and the density of the water each of which selectively passes through the coriolis meter.

In one exemplary embodiment, the dual component density sampler apparatus includes a water trap disposed between the dual-in-and-single-out manifold and the exit end of the exit tank. The water trap is structured to prevent water from the fluid mixture flowing from the dual-and-single-out manifold to the coriolis meter from displacing oil in the exit tank.

In another embodiment, the dual component density sample apparatus includes a temperature control apparatus coupled to at least the segregation tank apparatus. The temperature control apparatus is structured to equalize the temperature of the fluid mixture, the oil component, and the water component in the segregation tank apparatus with the temperature of the fluid mixture from the well so that the temperature of the fluid components from the segregation tank apparatus remain in thermal equilibrium with the tubing of the coriolis meter.

Several different arrangements for the temperature control apparatus can be included in the dual component density sampler apparatus. In one embodiment, a thermal insulation system is utilized which thermal insulation system surrounds each of the exterior walls of the entrance tank and exit tank of the segregation tank apparatus. In another embodiment, the thermal insulation system is integrated into the walls of the entrance and exit tanks of the segregation tank apparatus.

In another embodiment, the temperature control apparatus includes a system of production fluid piping disposed within at least one of the entrance tank and the exit tank. The production fluid piping receives and routes the same fluid mixture from the oil well through the segregation tank apparatus.

In another embodiment, the temperature control apparatus includes a system of co-axial production fluid piping disposed around at least one of the entrance tank and the exit tank of the segregation tank apparatus.

In another embodiment, the temperature control apparatus includes a resistive heater system which includes a resistive heating element and a temperature sensor. At least one of the tanks of the segregation tank apparatus, and in some instances both tanks, include a resistive heating system disposed in the interior of the tank to heat the fluid to the temperature measured by the coriolis meter.

There is also disclosed a method for determining a net oil quantity of a fluid mixture of oil and water from an oil well operation under production conditions. A dual component density sampler apparatus is disclosed, including a three-way valve, a dual-in-single-out manifold, a segregation tank apparatus and a coriolis meter structured to determine the net oil quantity of the fluid mixture from the oil well. The segregation tank apparatus includes an entrance tank and an exit tank.

The method may further include coupling the dual component density sampler apparatus to the oil well with a fluid mixture of oil and water from the oil well flowing into the three-way valve. The fluid mixture of oil and water from the oil well is routed from the three-way valve into the segregation tank apparatus to fill the segregation tank apparatus with the fluid mixture. Both tanks of the segregation tank apparatus are filled with the fluid mixture. The fluid mixture of oil and water from the three-way valve is routed to the coriolis meter through a dual-in-single-out manifold. The routing of the fluid mixture from the oil well is controlled by the three-way valve to either the segregation tank apparatus or the coriolis meter as determined by the user of the dual component density sampler apparatus.

Embodiments of the method allow sufficient time for the fluid mixture of oil and water in both the entrance tank and the exit tank to separate into an oil component and a water component in both the entrance tank and exit tank. The separation of the oil component and water component is a result of the effects of gravity on the different densities of the two immiscible components.

The disclosed method may also include routing the fluid mixture of oil and water from the oil well into the entrance tank of the segregation tank apparatus wherein the separated oil component in the entrance tank pushes the water component from the entrance tank into the exit tank of the segregation tank apparatus through an inter-tank connector. The water component from the entrance tank and the water component from the exit tank combined to push the oil component in the exit tank to the coriolis meter through the dual-and-single-out manifold.

In certain embodiments of the invention, the coriolis meter measures the density of the oil component pushed out of the exit tank by the force of the fluid moving through the inter-tank connector.

In a particular embodiment, the aforementioned method continues to route the fluid mixture of oil and water from the oil well into the entrance tank of the segregation tank apparatus wherein the separated oil component in the entrance tank pushes the water component from the entrance tank into the exit tank of the segregation apparatus through the inter-tank connector, with the water component from the entrance tank and water component from the exit tank combining to flow from the exit tank to the coriolis meter through the dual-and-single-out manifold. The coriolis meter then measures, before the oil component or fluid mixture from the entrance tank can mix with the water components exiting the exit tank, the density of the water components flowing through the coriolis meter.

In a further embodiment, the method continues to route the fluid flow from the three-way valve to the coriolis meter through the dual-and-single-out manifold and measures, in the coriolis meter, the density of the fluid mixture and the mass flow rate of the fluid mixture. Embodiments of the method then use the measured values of the density of the water component, density of the oil component from the exit tank, density of the fluid mixture, and the mass flow rate of the fluid mixture to calculate the net oil flowing in the fluid mixture.

The apparatus of the present invention is of a construction which is both reliable and long-lasting, and which requires little or no maintenance to be provided by the user throughout its operating lifetime. In some embodiments, the apparatus of the present invention is also of inexpensive construction to enhance its market appeal and to thereby afford it the broadest possible market.

Other aspects, objectives and advantages of the invention will become more apparent from the following detailed description when taken in conjunction with the accompanying drawings.

DESCRIPTION OF THE DRAWINGS

The accompanying drawings incorporated in and forming a part of the specification illustrate several aspects of the present invention and, together with the description, serve to explain the principles of the invention. In the drawings.

DETAILED DESCRIPTION OF THE EXEMPLARY EMBODIMENTS

Figure 1:
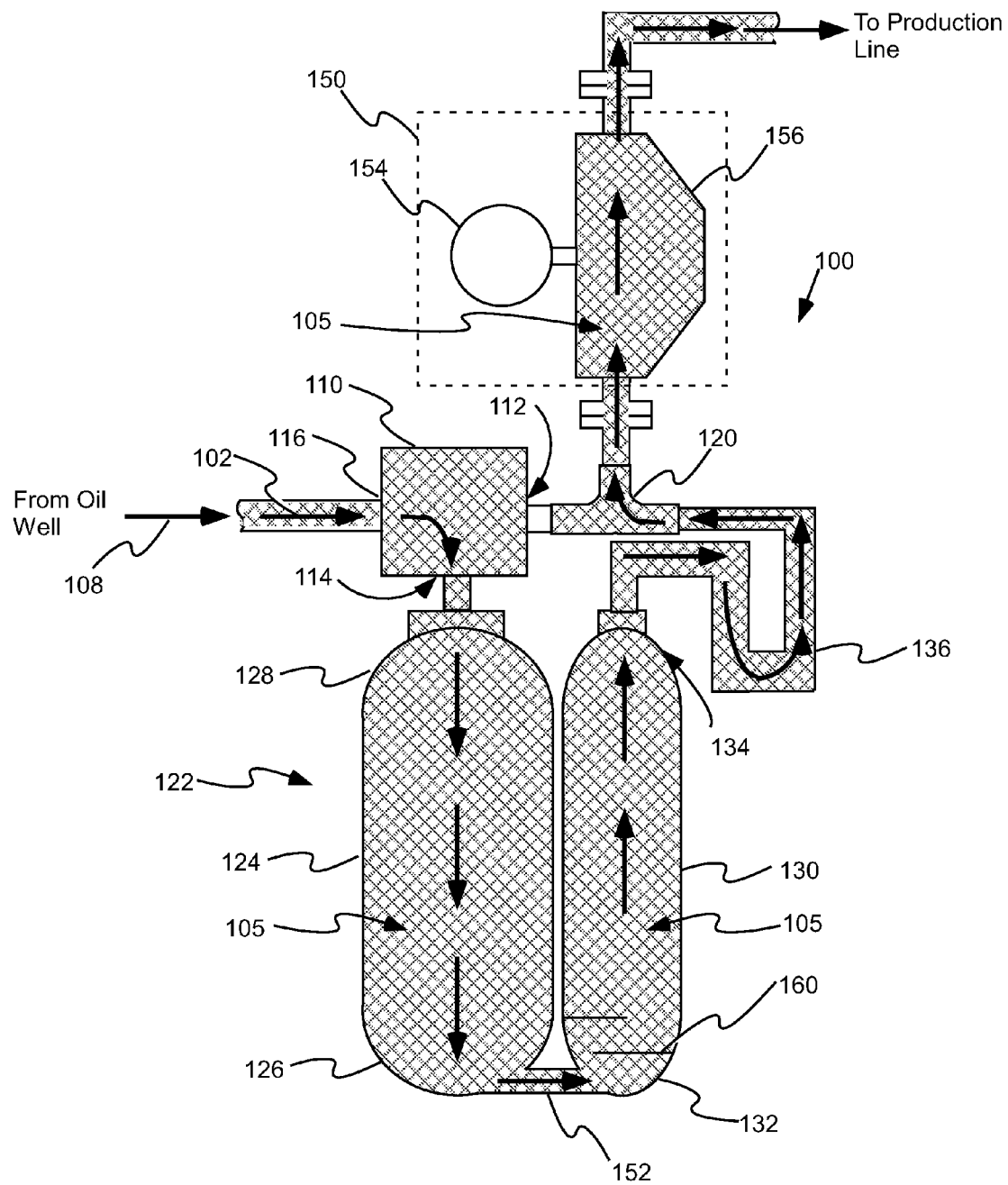
FIG. 1 is a schematic illustration of a dual component density sampler apparatus depicting a fluid mixture flow of oil and water from an oil well under well production conditions with the dual component density sampler apparatus filling a segregation tank apparatus, comprised of an entrance tank and an exit tank, with a mixture of oil and water, in accordance with an embodiment of the invention.

Referring to the FIGS. 1-9, there is disclosed a dual component density sampler apparatus 100 structured to determine at least one of a density of a water component 106 and a density of an oil component 104 of a fluid mixture 105 of oil and water extracted from a well. The well is typically an oil well. The dual component density sampler apparatus 100 determines the density of the water component 106 and the oil component 104 from the fluid mixture 105 while maintaining the dual component density sampler apparatus 100 in a production condition. The fluid mixture 105 coming from the well, more particularly from a gas separator apparatus (not shown) at a particular temperature and pressure, which is maintained in the dual component density sampler apparatus 100, to obtain an accurate value of net oil being extracted from the oil well.

The dual component density sampler apparatus 100 separates the oil and water under production conditions and flows the segregated fluids through a density-measuring device, such as a coriolis meter 150. It is envisioned that other types of density-measuring devices may be used in the scope of the present invention. However, for the sake of simplicity, a coriolis meter is used in the embodiments of the invention described herein. The coriolis meter 150 is structured to measure the net oil on the output of the oil well. The coriolis meter 150 determines at least one of the densities of the oil component 104 and water component 106, separately under process conditions and maintains those values, corrected for temperature and pressure, in reference densities stored in the coriolis meter 150. The frequency of this determination process and whether to determine at least one of the density of the oil component 104 and the density of water component 106 is based on which component's density is subject to change and how rapidly it is changing.

As illustrated in FIGS. 1-4, the dual component density sampler apparatus 100 is structured with a three-way valve 110, a dual-in-single-out manifold 120, a segregation tank apparatus 122, and a coriolis meter 150. Appropriate piping systems interconnect the various components as will be described below. The apparatus and method for determining a net oil quantity of a fluid mixture 105 of oil and water from an oil well operation under production conditions, includes a dual component density sampler apparatus 100 including a three-way valve 110. The apparatus includes a dual-in-single-out manifold 120 coupled to the three-valve 110. The three-way valve 110 is also coupled to a segregation tank apparatus 122 with piping systems routing fluid to a coriolis meter 150.

Referring to FIG. 1, the figure illustrated the schematic diagram of an exemplary embodiment of the dual component density sampler apparatus 100. The fluid mixture flow 102 from the oil well or gas separator 108 coupled to an oil well flows into the three-way valve 110. The three-way valve includes an input port 116, a first output port 112 and a second output port 114. The second output port 114 is coupled to an entrance tank 124 of the segregation tank apparatus 122. The first output port 112 of the three-way valve 110 is coupled, in a fluid communication, with the dual-in-single-out manifold 120. The three-way valve 110 operated either manually or automatically by remote connections, routes the fluid mixture flow 102 from the well to either the segregation tank apparatus 122 or the coriolis meter 150.

The segregation tank apparatus 122 functions to separate the water component 106 and the oil component 104 of the fluid mixture 105 entering the segregation tank apparatus 122. The entrance tank 124 includes an entrance end 128 which is coupled to the second output port 114. An exit end 126 of the entrance tank 124 is coupled to an entrance end 132 of an exit tank 130 of the segregation tank apparatus 122. The entrance end 132 of the exit tank 130 may contain one or more baffles 160 to reduce the velocity of any fluid flow in the segregation tank and prevent mixing of the segregated oil and water components. An exit end 134 of the exit tank 130 is coupled to the dual-in-single-out manifold 120.

The volume of the entrance tank 124 may be different from the volume of the exit tank 130. The volumetric difference between the entrance tank 124 and the exit tank 130 will be explained below in reference to FIGS. 1-4. In the specific embodiments of FIGS. 1-4, the volume of the entrance tank 124 is greater than the volume of the exit tank 130. However, the relationship of the entrance and exit tank volumes may differ in alternate embodiments of the invention.

Still referring to FIG. 1, fluid in the segregation tank apparatus 122 flows from the exit end 134 of the exit tank 130 through a water trap 136 into the dual-in-single-out manifold 120. The water trap 136 is structured to prevent water from the fluid mixture 105 flowing from the dual-in-single-out manifold 120 to the coriolis meter 150 from displacing segregated oil in the exit tank 130.

The fluid moving through the dual-in-single-out manifold 120 from either the three-way valve 110 or the segregation tank apparatus 122 moves from the dual-in-single-out manifold 120 to the coriolis meter 150. The coriolis meter 150 includes an electronic section 154 and a flow section 156. The mass flow rate and density measurements of fluid moving through the coriolis meter 150 are determined by the coriolis meter 150. The temperature and pressure of fluid moving through the coriolis meter 150 are determined by separate sensors and the results are input to the electronic section 154. The fluid mixture 105 continues on from the coriolis meter 150 to a production line for further processing.

During operation, as illustrated in FIG. 1, after the dual component density sampler apparatus 100 is coupled to the oil well, a fluid mixture 105 of oil and water from the oil well flows into the three-way valve 110. When it is determined that the sampling process should occur, three-way valve 110 routes the fluid mixture 105 from the oil well from the three-way valve 110 into the segregation tank apparatus 122 to fill the segregation tank apparatus 122 with the fluid mixture 105. This fluid flow 102 is maintained until both tanks, the entrance tank 122 and exit tank 130, including the inter-tank connector 152 which couples the exit end 126 of the entrance tank 122 and the entrance end 132 of the exit tank 130, are completely filled with a current sample of the fluid mixture 105.

Figure 2:
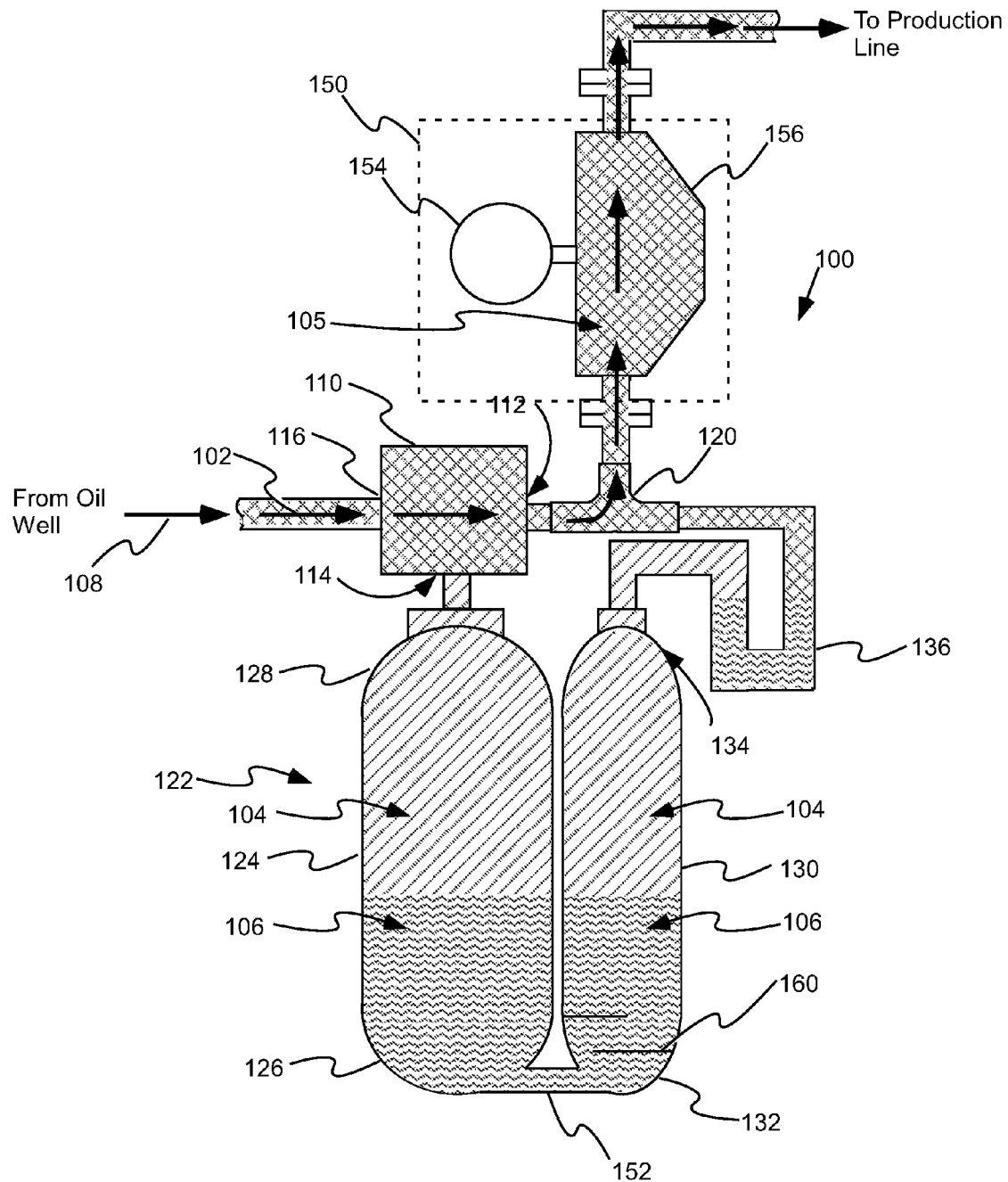
FIG. 2. is a schematic illustration of the dual component density sampler apparatus of FIG. 1 depicting a separation of oil and water in the segregation tank apparatus after a three-way valve closes off fluid flow from the oil well to the segregation tank apparatus.

FIG. 2. is a schematic illustration of the dual component density sampler apparatus 100 of FIG. 1 depicting the separation of oil and water in the segregation tank apparatus 122 after the three-way valve 110 closes off fluid flow 102 from the oil well to the segregation tank apparatus 122. In the embodiment shown, the three-way valve 110 then routes the fluid flow 102 from the first output port 112 of the three-way valve 110, to the coriolis meter 150 through the dual-in-single-out manifold 120, wherein the coriolis meter 150 measures the density and mass flow rate of the fluid mixture 105 of oil and water. During that step, the fluid mixture 105 of oil and water in the segregation tank apparatus 122 is allowed to separate into an oil component 104 and a water component 106. Because the oil component 104 typically has a density that is less than that of the water component 106, the oil component 104 will separate from the water component 106, the oil component 104 rising to the top of the entrance and exit tanks 124, 130, due to the effects of gravity.

Figure 3:
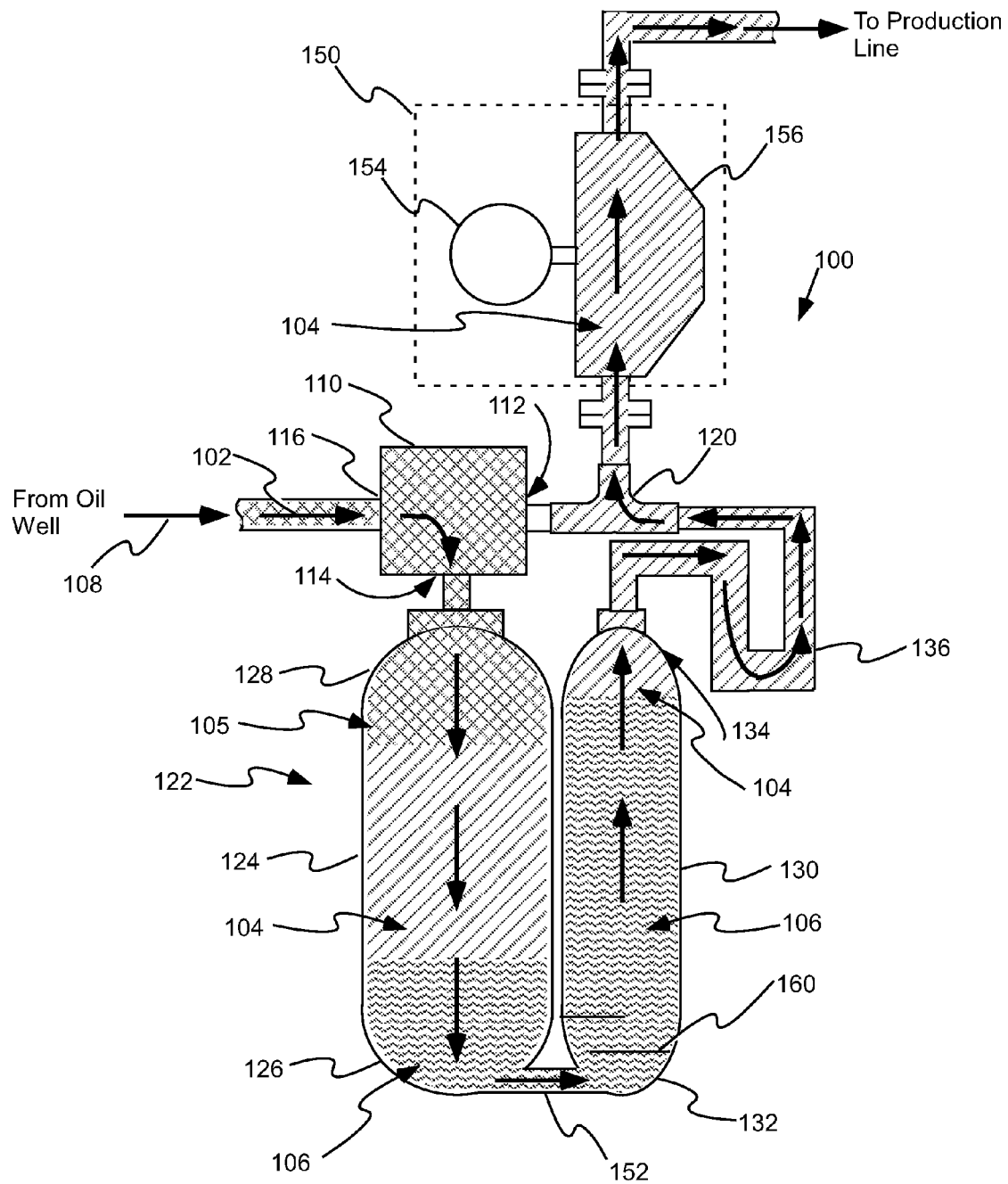
FIG. 3 is a schematic illustration of the dual component density sampler apparatus of FIG. 1 depicting fluid flow from the three-way valve to the segregation tank apparatus with the mixture of oil and water in an entrance tank of the segregation tank apparatus pushing the segregated oil out of an exit tank of the segregation tank apparatus through a coriolis meter.

FIG. 3 is a schematic illustration of the dual component density sampler apparatus 100 of FIG. 1 depicting fluid flow 102 from the three-way valve 110 to the segregation tank apparatus 122 with the mixture of oil and water, in the entrance tank 124, pushing the segregated oil out of the exit tank 130 through the coriolis meter 150. After a sufficient time period has passed to allow the separation of the oil component 104 and water component 106, the three-way valve 110 again routes the fluid mixture 105 of oil and water into the segregation tank apparatus 122. The fluid mixture 105 of oil and water pushes the oil component 104 in the entrance tank and the water component 106 in the entrance tank through the inter-tank connector 152 into the exit tank 130. The water component 106 from the entrance tank 124 and the water component 106 from the exit tank 130 combine to push the oil component 104 in the exit tank 130 through the water trap 136 and through the dual-in-single-out manifold 120 to the coriolis meter 150. The coriolis meter 150 measures the density of the oil component 104 being pushed from the exit tank 130. In one embodiment, the coriolis meter 150 also calculates what the density of the oil component 104 would be at standard temperature and pressure.

Figure 4:
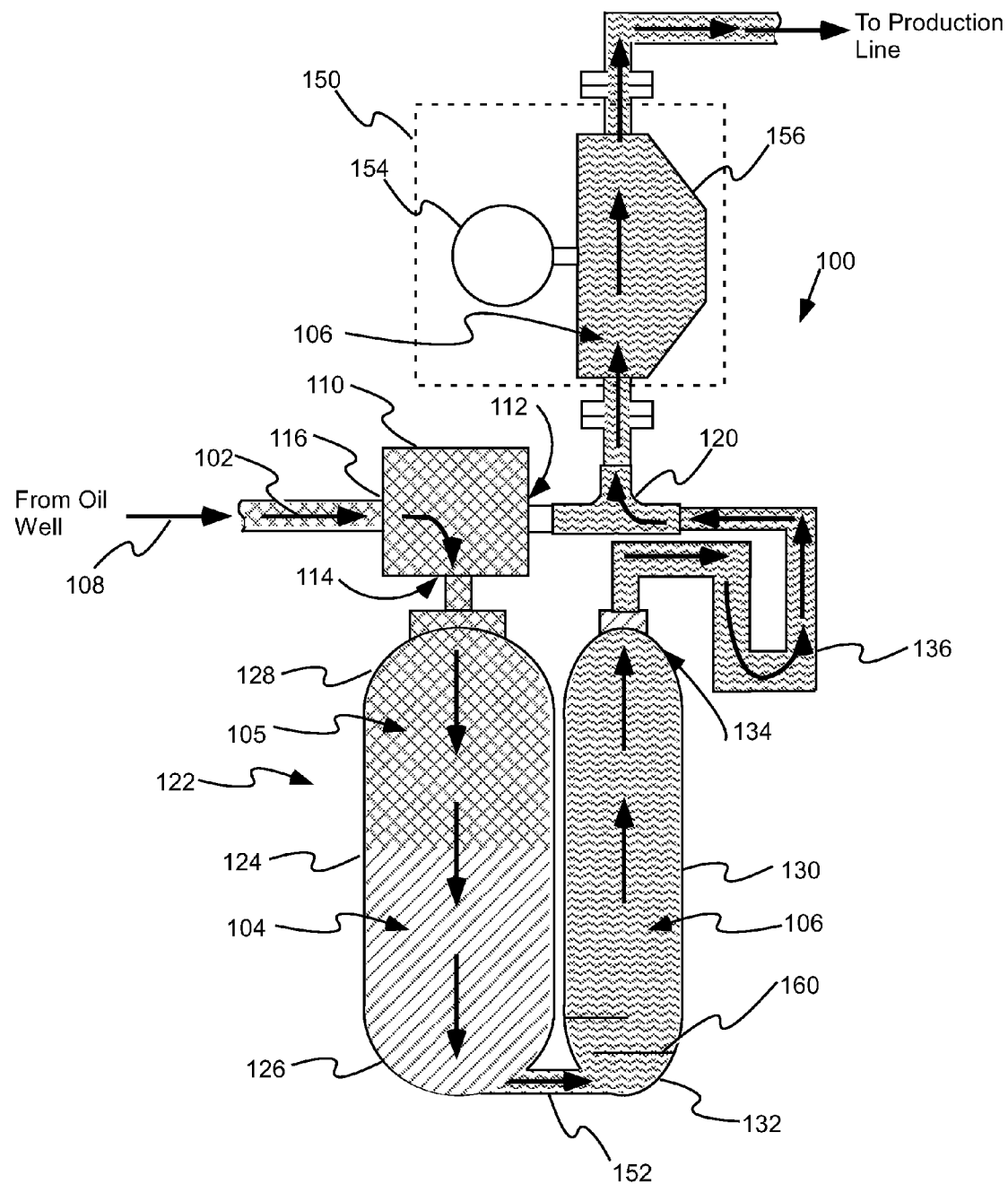
FIG. 4 is a schematic illustration of the dual component density sampler apparatus of FIG. 1 depicting fluid flow from the three-way valve to the segregation tank apparatus with the mixture of oil and water in an entrance tank of the segregation tank apparatus pushing the segregated water out of an exit tank of the segregation tank apparatus through the coriolis meter before any oil from the entrance tank enters the exit tank.

FIG. 4 is a schematic illustration of the dual component density sampler apparatus 100 of FIG. 1 depicting fluid flow 102 from the three-way valve 110 to the segregation tank apparatus 122 with the mixture of oil and water, in the entrance tank 124, pushing the segregated water out of the exit tank 130 through the coriolis meter 150 before any oil from the entrance tank 124 enters the exit tank 130. In this embodiment, the three-way valve 110 continues to route the fluid mixture 105 of oil and water from the oil well into the entrance tank 124 of the segregation tank apparatus 122. The fluid mixture 105 of oil and water pushes the oil component 104 in the entrance tank 124, which in turn pushes the water component 106 from the entrance tank 124 into the exit tank 130 of the segregation tank apparatus 122 through the inter-tank connector 152.

The water component 106 in the entrance tank and the water component 106 from the exit tank 130 combine to flow from the exit tank 130 to the coriolis meter 150 through the dual-in-single-out manifold 122. The water (shown in FIG. 4) exiting from the exit tank 130 through the dual-in-single-out manifold 120 flows into the coriolis meter 150 where the coriolis meter 150 measures the density of the water component 106. In one embodiment, the coriolis meter 150 also calculates what the density of the water component 106 would be at standard temperature and pressure. This measurement of density for the oil component 104 and the water component 106 may be performed automatically at defined intervals, such as once a day, or upon occurrence of some event such as chemical treatment of the well or a restart after a period in which no production occurs or may be performed upon manual activation by the well operator.

When the system is not acquiring a sample or measuring the density for the oil component 104 and the water component 106, the three-way valve 110 routes the fluid flow 102 to the coriolis meter 150 through the dual-in-single-out manifold 120 and the coriolis meter 150 measures the mass flow rate and density of the fluid mixture 105 of oil and water, with measurements of the pressure and temperature of the fluid mixture 105 of oil and water being input to the electronic section 154 from external sensors. Using the previously measured densities of the oil component 104 and the water component 106 and applying methods known in the art to compensate for pressure and temperature differences, the system calculates the net oil produced.

The dual component density sampler apparatus 100 is structured to measure the water component 106 as described above in the coriolis meter 150 before the oil component 104 or the fluid mixture 105 from the entrance tank 124 can mix with the water component 106 exiting the exit tank 130. It is for that reason that the entrance tank 124 may be of a different size than the exit tank 130. The volumetric sizing calculations for the entrance tank 124 and the exit tank 130 depends in part on the expected range of ratios of oil to water in the fluid mixture of oil and water and the terminal velocity of the largest oil droplets that rise through the segregated water component 106 when the oil at the top of the entrance tank 124 flows through the inter-tank connector 152 into the exit tank 130 during the density measurement of the water component 106 in the coriolis meter 150.

Referring now to FIGS. 5-9, in some embodiments, the dual component density sampler apparatus 100 also includes a temperature control apparatus 138 coupled to at least the segregation tank apparatus 122. The temperature control apparatus 138 is structured to equalize the temperature of the fluid mixture 105, the oil component 104, and the water component 106 in the segregation tank apparatus 122 with the temperature of the fluid mixture 102 from the well. It is found that the temperature changes of any fluid in the dual component density sampler apparatus 100 have to be equalized with the temperature of the fluid mixture flow 102 from the oil well. Heat may be gained or lost through the various components and through various thermodynamic mechanisms, resulting in a temperature change and several temperature control apparatus 138 configurations may be utilized to equalize the temperature of the fluid from the oil well 102 with the various fluids passing through the dual component density sampler apparatus 100.

Figure 5:
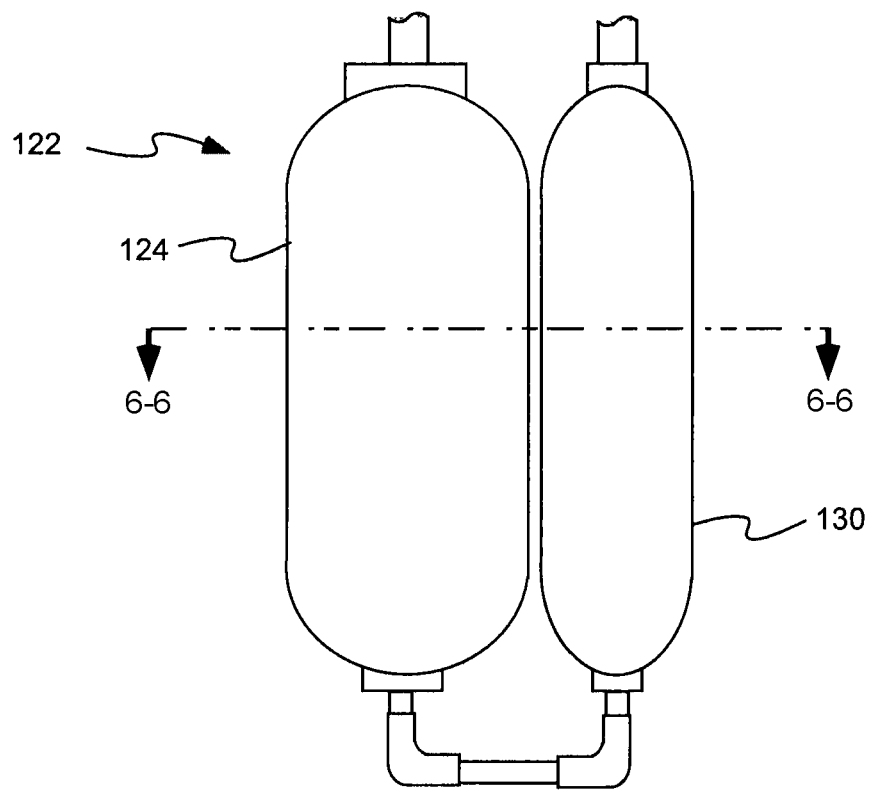
FIG. 5 is a schematic illustration of the dual component density sampler apparatus of FIG. 1 depicting the segregation tank apparatus with the entrance tank defining a volume different than the volume of the exit tank.
Figure 6:
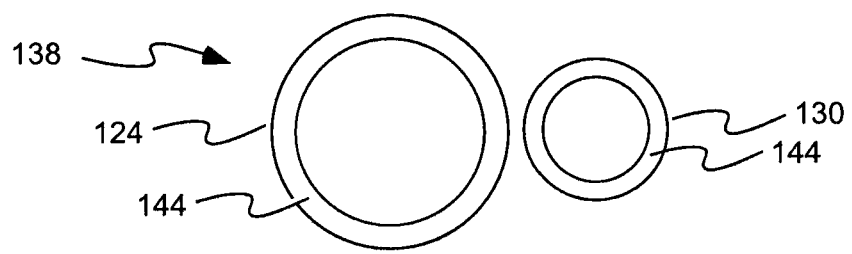
FIG. 6 is a cross-sectional view of the segregation tank apparatus of FIG. 5 that illustrates a thermal insulation type of temperature control apparatus.

FIG. 6 is a cross-sectional view of the segregation tank apparatus 122 of FIG. 5 that illustrates a thermal insulation type 144 of temperature control apparatus 138. As will be explained below, several different arrangements for the temperature control apparatus 138 can be included in the apparatus 100. In the embodiment of FIG. 6, the thermal insulation system 144 surrounds each of the exterior walls of the entrance tank 124 and the exit tank 130. In alternate embodiments, the thermal insulation system 144 is integrated into the walls of the entrance tank 124 and exit tank 130.

Figure 7:
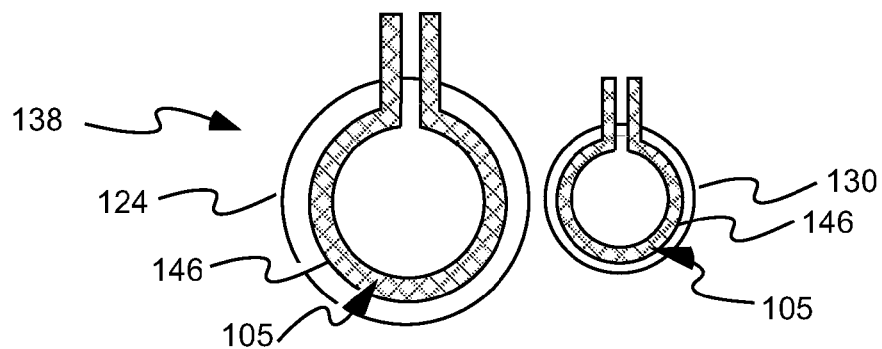
FIG. 7 is a cross-sectional view of the segregation tank apparatus of FIG. 5 that illustrates an internal piping production fluid type of temperature control apparatus.

FIG. 7 is a cross-sectional view of the segregation tank apparatus 122 of FIG. 5 that illustrates an internal production fluid piping 146 type of temperature control apparatus 138. In this embodiment, the temperature control apparatus 138 includes the system of production fluid piping 146 disposed within at least one of the entrance tank 124 and the exit tank 130. The fluid mixture flow 102 from the well is routed to the interior of the entrance tank 124 and the exit tank 130, thereby using the heat from the fluid mixture flow 102 to heat or cool, depending on the ambient temperature, the oil component 104 and water component 106 and fluid mixture 105 of oil and water in the segregation tank apparatus 122.

Figure 8:
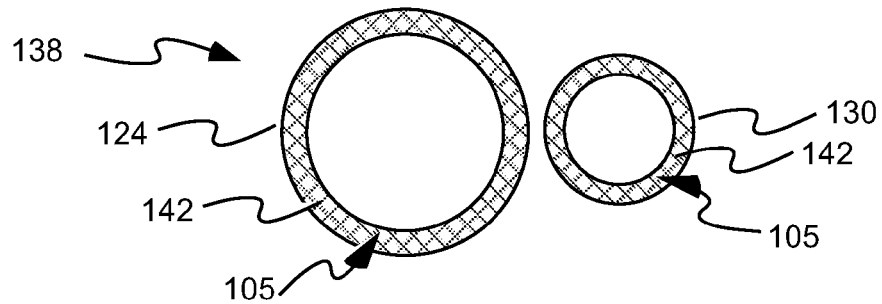
FIG. 8 is a cross-sectional view of the segregation tank apparatus of FIG. 5 that illustrates a coaxial production fluid piping type of temperature control apparatus.

FIG. 8 is a cross-sectional view of the segregation tank apparatus 122 of FIG. 5 that illustrates a coaxial production fluid piping 142 type of temperature control apparatus 138. In this embodiment, the temperature control apparatus 138 includes the system of coaxial production fluid piping 142 disposed around the exterior of at least one of the entrance tank 124 and exit tank 130 of the segregation tank apparatus. In this case, the production fluid mixture flow 102 surrounds the interior walls of the entrance tank 124 and exit tank 130 to equalize the temperature between any fluid in the tanks of the segregation tank apparatus 122 with the fluid mixture flow from the well 102.

Figure 9:
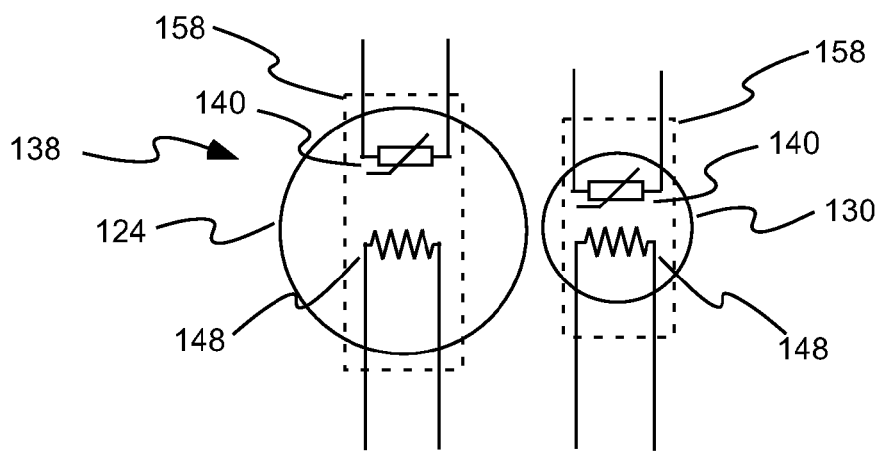
FIG. 9 is a cross-sectional view of the segregation tank apparatus of FIG. 5 that illustrates a temperature control apparatus comprising a resistive heating element and a temperature sensor.

FIG. 9 is a cross-sectional view of the segregation tank apparatus 122 of FIG. 5 that illustrates a temperature control apparatus 138 comprising a resistive heating element 148 and a temperature sensor 140. In this embodiment, the temperature control apparatus 138 includes a resistive heater system 158. The resistive heater system 158 includes the aforementioned resistive heating element 148 and the temperature sensor 140. The temperature sensor 140 measures the temperature of the fluid in either or both of the entrance tank 124 and exit tank 130 and a controller adjusts the current flowing through the resistive heating element 148 to adjust the temperature of any fluid in the segregation tank apparatus 122. Control of the various temperature control apparatus 138 can be done manually or automatically as determined by a user utilizing conventional methods. Whatever the control method employed, the desired result is to match the temperatures in the segregation tank apparatus 122 with the temperature measured by the coriolis meter 150.

The controller can be coupled to the dual component density sampler apparatus 100 to control the various functions of the apparatus 100. The controller may be housed within the coriolis meter electronic section 154 or be a microprocessor coupled to the various components of the system. The controller may also be a server coupled to an array of peripherals or a desktop computer, or a laptop computer, or a smart-phone. It is also contemplated that the controller is configured to control or monitor individual valves, heaters, sensors, etc. associated with the apparatus 100. The controller may be remote from any of the apparatus.

Communication between the controller and the various apparatus may be either by hardwire or wireless devices. A memory/data base coupled to the controller may be remote from the controller. The controller typically includes an input device, for example a mouse, or a keyboard, and a display device, for example a monitor screen or a smart phone. Such devices can be hardwired to the controller or connected wirelessly with appropriate software, firmware, and hardware.

The display device may also include a printer coupled to the controller. The display device may be configured to mail or fax reports as determined by a user. The controller may be coupled to a network, for example, a local area network or a wide area network, which can be one of a hardwire network and a wireless network, for example a Bluetooth network or internet network, for example, by a WI-FI connection or "cloud" connection.

For purposes of this disclosure, the term "coupled" means the joining of two components (electrical, electromagnetic or mechanical) directly or indirectly to one another. Such joining may be stationary in nature or moveable in nature. Such joining may be achieved with the two components (electrical, electromagnetic or mechanical) and any additional intermediate members being integrally formed as a single unitary body with one another or the two components and any additional member being attached to one another. Such adjoining may be permanent in nature or alternatively be removable or releasable in nature.

Although the foregoing description of the present disclosure has been shown and described with reference to particular embodiments and applications thereof, it has been presented for purposes of illustration and description and is not intended to be exhaustive or to limit the disclosure to the particular embodiments and applications disclosed. It will be apparent to those having ordinary skill in the art that a number of changes, modifications, variations, or alterations to the invention as described herein may be made, none of which depart from the spirit or scope of the present disclosure. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A dual component density sampler apparatus for determining at least one of a density of a water component and a density of an oil component of a fluid mixture of oil and water extracted from an oil well while maintaining the components in production conditions, the dual component density sampler apparatus comprising:
   a three-way valve coupled to the oil well during production flow of fluid from the oil well at an input port, with the three-way valve having a first output port and a second output port;
   a dual-in-single-out manifold coupled to the first output port;

a segregation tank apparatus for separating the water component and the oil component of the fluid mixture, said segregation tank apparatus comprising an entrance tank and an exit tank wherein:
  an entrance end of the entrance tank is coupled to the second output port;
  an exit end of the entrance tank coupled to an entrance end of the exit tank; and
  an exit end of the exit tank coupled to the dual-in-single-out manifold; and
a coriolis meter coupled to the dual-in-single-out manifold, the coriolis meter configured to selectively measure a density of the fluid mixture, a density of the oil component, and a density of the water.

2. The dual component density sampler apparatus of claim 1, wherein a volume of the entrance tank is different from a volume of the exit tank.

3. The dual component density sampler apparatus of claim 1, further comprising a water trap disposed between the dual-in-single-out manifold and the exit end of the exit tank, the water trap configured to prevent water from the fluid mixture, flowing from the dual-in-single-out manifold to the coriolis meter, from displacing the oil component in the exit tank.

4. The dual component density sampler apparatus of claim 1, further comprising a temperature control apparatus coupled to the segregation tank apparatus, the temperature control apparatus configured to equalize a temperature of the fluid mixture, the oil component, and the water component in the segregation tank apparatus with the temperature of the fluid mixture from the well.

5. The dual component density sampler apparatus of claim 4, wherein the temperature control apparatus comprises a thermal insulation system.

6. The dual component density sampler apparatus of claim 4, wherein the temperature control apparatus comprises a system of production fluid piping disposed within at least one of the entrance tank and the exit tank.

7. The dual component density sampler apparatus of claim 4, wherein the temperature control apparatus comprises a system of coaxial production fluid piping disposed around at least one of the entrance tank and the exit tank.

8. The dual component density sampler apparatus of claim 4, wherein the temperature control apparatus comprises a resistive heater system, wherein said resistive heater system comprises a resistive heating element and a temperature sensor.

9. The dual component density sampler apparatus of claim 1, wherein the exit end of the entrance tank is coupled to the entrance end of the exit tank via an inter-tank connector.

10. The dual component density sampler apparatus of claim 1, wherein the entrance end of the exit tank includes one or more baffles to reduce a velocity of fluid flowing through the segregation tank apparatus, and to prevent mixing of segregated oil and water components.

11. A method for determining a net oil quantity of a fluid mixture of oil and water from an oil well operating under production conditions with a dual component density sampler apparatus, the method comprising:
  coupling the dual component density sampler apparatus to the oil well with a fluid mixture of oil and water from the oil well flowing into a three-way valve, the dual component density sampler apparatus including the three-way valve, a dual-in-single-out manifold, a segregation tank apparatus and a coriolis meter, wherein the segregation tank apparatus comprises an entrance tank and an exit tank;
  routing the fluid mixture from the three-way valve into the segregation tank apparatus to fill the segregation tank apparatus with said fluid mixture, wherein routing the fluid mixture from the three-way valve into the segregation tank comprises routing the fluid mixture into the entrance tank, and from the entrance tank into the exit tank;
  allowing sufficient time for the fluid mixture of oil and water in both the entrance tank and the exit tank to separate into an oil component and a water component in both the entrance tank and the exit tank, wherein the separated oil component in the entrance tank pushes the water component from the entrance tank into the exit tank of the segregation tank apparatus, with the water component from the entrance tank and the water component in the exit tank combining to push the oil component in the exit tank to the coriolis meter through the dual-in-single-out manifold;
  measuring, in the coriolis meter, the density of the oil component from the exit tank;
  routing the fluid mixture of oil and water from the oil well into the entrance tank of the segregation tank apparatus such that the separated oil component in the entrance tank pushes the water component from the entrance tank into the exit tank of the segregation tank apparatus, with the water component from the entrance tank and the water component from the exit tank combining to flow from the exit tank to the coriolis meter through the dual-in-single-out manifold;
  measuring, before the oil component or fluid mixture from the entrance tank can mix with the water components exiting the exit tank, the density of the water component flowing through the coriolis meter;
  routing the fluid mixture from the three-way valve to the coriolis meter through the dual-in-single-out manifold;
  measuring, in the coriolis meter, the density and the mass flow rate of the fluid mixture; and
  using the measured values of the densities of the water component, of the oil component, and of the fluid mixture, along with the mass flow rate of the fluid mixture, to calculate the net oil flowing in the fluid mixture.

12. The method of claim 11, wherein the volume of the entrance tank is greater than the volume of the exit tank.

13. The method of claim 11, further comprising controlling a temperature of the fluid mixture, the oil component, and the water component in the segregation tank apparatus to reduce any difference between the temperature of the fluid mixture, the oil component, and the water component in the segregation tank apparatus, and that of the fluid mixture of oil and water flowing from the oil well.

14. The method of claim 13, wherein controlling the temperature of the fluid mixture, the oil component, and the water component in the segregation tank apparatus comprises wherein controlling the temperature of the fluid mixture, the oil component, and the water component in the segregation tank apparatus with a temperature control apparatus coupled to the segregation tank apparatus.

15. The method of claim 14, wherein controlling the temperature of the fluid mixture, the oil component, and the water component in the segregation tank apparatus with a temperature control apparatus comprises controlling the temperature of the fluid mixture, the oil component, and the water component in the segregation tank apparatus with a thermal insulation system.

16. The method of claim 14, further comprising directing the fluid mixture to flow through the temperature control apparatus, which comprises a system of production fluid piping disposed within at least one of the entrance tank and the exit tank.

17. The method of claim 14, further comprising directing the fluid mixture to flow through the temperature control apparatus, which comprises a system of coaxial production fluid piping disposed around at least one of the entrance tank and the exit tank.

18. The method of claim 14, wherein the temperature control apparatus comprises a resistive heater system comprising a resistive heating element and a temperature sensor, the method further comprising controlling the heater element to maintain a measured temperature from the temperature sensor that is the same as a measured temperature from the coriolis meter.

19. The method of claim 11, wherein the water component is pushed from the entrance tank into the exit tank of the segregation tank apparatus through an inter-tank connector.

20. The method of claim 11, further comprising reducing the velocity of fluid flow through the segregation tank, and preventing a mixing of segregated oil and water components by arranging one or more baffles in the entrance end of the exit tank.

* * * * *